US00PP23701P3

(12) United States Plant Patent
Schoone

(10) Patent No.: US PP23,701 P3
(45) Date of Patent: Jul. 2, 2013

(54) ***PHALAENOPSIS* ORCHID PLANT NAMED 'PACIFIC POINT'**

(50) Latin Name: ***Phalaenopsis* hybrid**
Varietal Denomination: Pacific Point

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 13/137,258

(22) Filed: Aug. 1, 2011

(65) Prior Publication Data

US 2012/0102609 P1 Apr. 26, 2012

(30) Foreign Application Priority Data

Oct. 20, 2010 (NL) ..... PBR OPS708

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP

(57) ABSTRACT

A new and distinct *Phalaenopsis* plant named 'Pacific Point' particularly characterized by flowers which are purple with a white blush in the center and some white and yellow at the labellum; plants which may be propagated economically and uniformly using tissue culture; plants which produce more than one inflorescence; long and sturdy inflorescences; and dark-green foliage.

3 Drawing Sheets

Latin name of the genus and species of the plant claimed: *Phalaenopsis* hybrid.

Variety denomination: 'Pacific Point'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Pacific Point'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Pacific Point' is a product of a controlled breeding program conducted by the inventor, Rene Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Pacific Point' originated from a cross made by the inventor in 1998 in Strengweg, Heemskerk, The Netherlands. The female or seed parent is the *Phalaenopsis* cultivar designated 'Leen Boon', unpatented. The male or pollen parent is the *Phalaenopsis* cultivar designated 'Zuma Diadem'×'Malibu Meadow', unpatented. The new *Phalaenopsis* 'Pacific Point' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in January, 2006 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Pacific Point', which in combination distinguish this *Phalaenopsis* as a new and distinct cultivar:

1. flowers which are purple with a white blush in the center and some white and yellow in the labellum.
2. plant produces more than one inflorescence;

3. plants may be propagated economically and uniformly using tissue culture;
4. inflorescences are long and sturdy; and
5. dark-green foliage.

When compared to its parental cultivars, the flowers of 'Pacific Point' are violet purple, but lighter than in either of its parental cultivars. Its female parent 'Leen Boon' has similar but darker violet purple colored flowers. Its male parent, 'Zuma Diadem'×'Malibu Meadow', which is a cross-breeding between a white flower with a red labellum and a violet/purple colored flower, also has darker violet purple flowers than 'Pacific Point'.

Presently, there is no other commercial cultivar to which 'Pacific Point' can be meaningfully compared.

BRIEF DESCRIPTION OF THE PHOTOGRAPHS

The accompanying photographs illustrate the overall appearance of the new *Phalaenopsis* 'Pacific Point' showing the colors as true as is reasonably possible with colored reproductions of this type. Colors in the photographs may differ slightly from the color values cited in the detailed botanical description, which accurately describe the color of 'Pacific Point'.

DETAILED BOTANICAL DESCRIPTION

Figure 1:
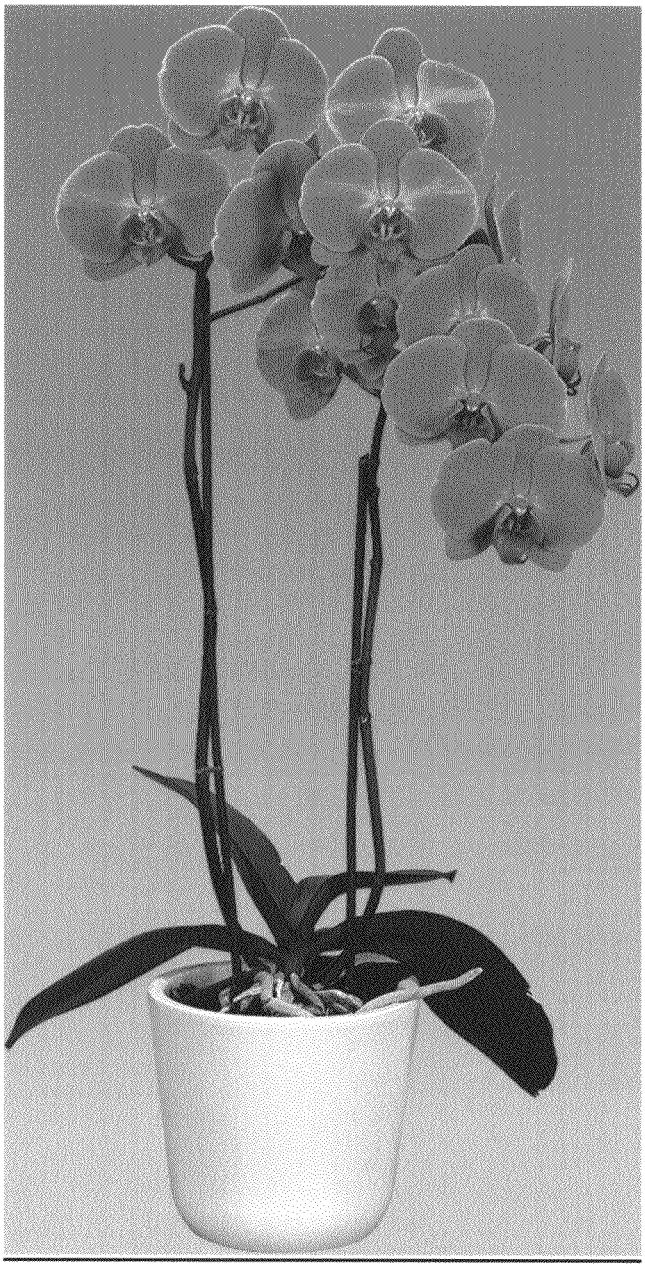
FIG. 1 shows a side view perspective of a typical flowering plant of 'Pacific Point' in a 12 cm pot, at 16 months of age.

The new *Phalaenopsis* cultivar 'Pacific Point' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Pacific Point' as grown in a greenhouse in Strengweg, Heemskerk, The Netherlands, under conditions which closely approximate those generally used in commercial practice. Initially, the ideal temperature to grow plants of 'Pacific Point' is 27° C. during the day and at night. Then, during the flowering phase of 'Pacific Point', the ideal growing temperature is 20-22° C. during the day and 18° C. at night: Light levels for growing 'Pacific Point' are a minimum of 5,000 lux and a maximum of 10,000 lux. A balanced fertilizer with level of 200 ppm N, 87 ppm P, 168 ppm K is applied. Duration of growth of 'Pacific Point' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Pacific Point' plants described is 12 months after potting.

Classification:

*Botanical.*—*Phalaenopsis* hybrid.

Parentage:

*Female or seed parent.*—*Phalaenopsis* cultivar designated 'Leen Boon' (unpatented).

*Male or pollen parent.*—*Phalaenopsis* cultivar designated 'Zuma Diadem'×'Malibu Meadow' (unpatented).

Propagation:

*Type.*—Tissue culture.

*Rooting habit and description.*—Fleshy; approximately 5 mm-7 mm wide and green in color; freely branching. It takes 12 weeks for plants growing in tissue culture to initiate roots.

Plant:

*Size at maturity.*—Height: about 57 cm. Spread: about 30 cm to 40 cm.

*Growth habit.*—Standard; dark-green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture (upper & underside).*—Smooth and leathery.

*Pubescence.*—3 to 4 pairs of leaves.

*Mature leaf length.*—About 15 to 18 cm.

*Mature leaf width.*—About 6 to 8 cm.

*Mature leaf thickness.*—About 2 mm.

*Mature leaf color.*—upper side: RHS N137A; under side: RHS 138A with purple RHS N79A edges.

*Leaf base.*—Acute.

*Margin.*—Entire.

*Venation.*—Pattern: parallel. Color of midvein: upper side: dark green RHS N137A; under side: green RHS 138A and a little purple RHS N79A.

Raceme:

*Quantity per plant.*—About 1 to 2.

*Number of flowers per peduncle.*—About 6 to 12.

*Length.*—About 50 to 60 cm.

*Diameter.*—About 5 mm.

*Strength.*—Strong.

*Aspect.*—Upright.

*Texture.*—Glabrous and smooth.

*Color.*—Dark green RHS N137A with some RHS 144B.

*Internode.*—Length: about 40 mm to 45 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 20 mm to 25 mm. Diameter (at midpoint): about 15 mm to 20 mm. Shape: egg-shaped. Color: green RHS 146C and purple RHS N78B.

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
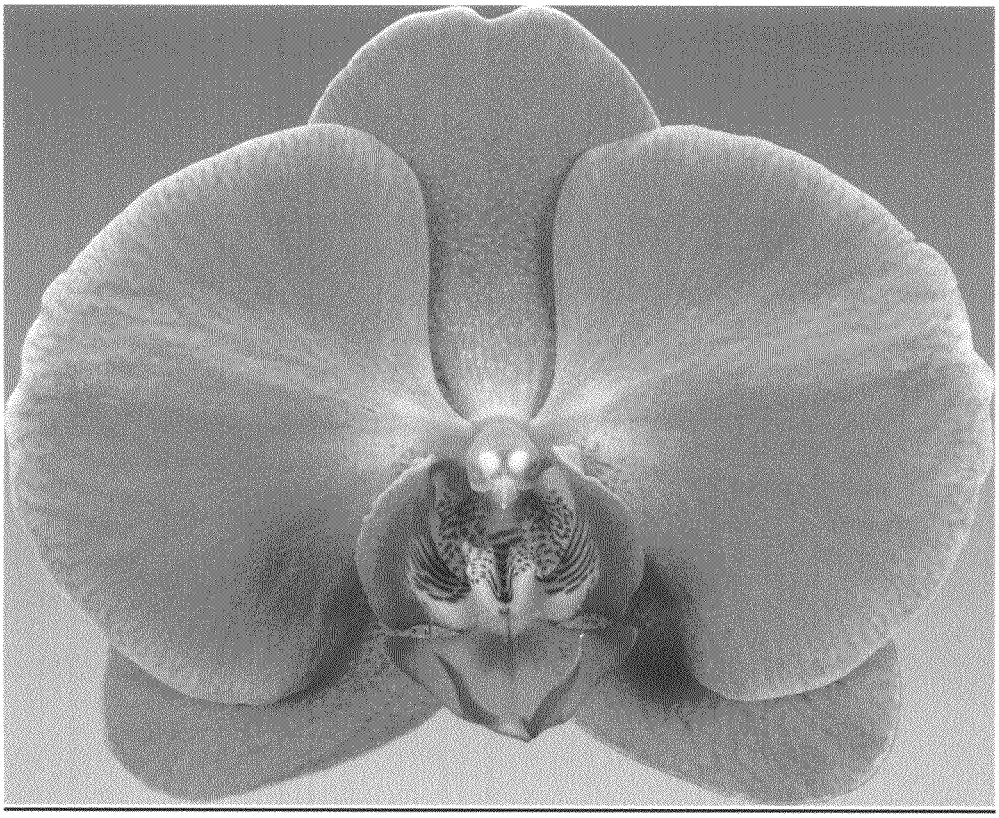
FIG. 2 shows a close-up view of the typical buds and flowers of 'Pacific Point'.
Figure 3:
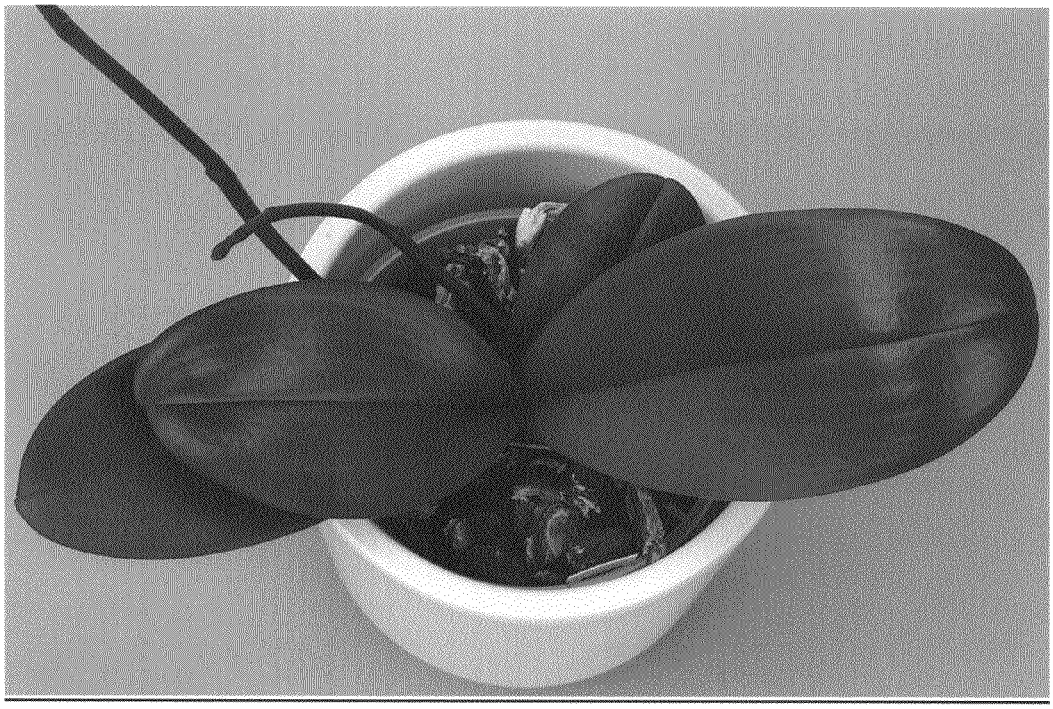
FIG. 3 shows a close-up view of the typical leaves of 'Pacific Point'.

*Flower*.—Rate of opening: Flowers fully opened about 2 to 3 days after petal and sepal separation. Orientation at opening: slanted upward and outward. Shape: see FIG. 2. Size: Height: about 75 mm. Diameter: about 93 mm. Depth of tube: about 15 mm.

*Petals*.—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate and weakly cupped. Apex: oval. Margin: entire and weakly undulate. Base: broadly ovate. Length: about 56 mm. Width: about 40 mm. Texture: Upper surface: smooth and satiny. Under surface: smooth and satiny. Color (when fully opened): Upper side: Main color is purple RHS N78B, with a white blush RHS NN155C in the center. Under side: purple RHS N78C. Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: Lateral lobes: oval. Midlobe: slightly pointed. Length: about 32 mm. Width (not flattened): about 26 mm. Texture: Upper & under surface: smooth and satiny. Color (when fully opened): Upper surface: The main color is purple/violet RHS N78A. The base of the lateral lobes is white RHS NN155C with purple/red stripes and spots RHS 64A. From the base on the under edges also some orange/purple RHS N34A. Midlobe is purple/violet RHS N78A. Upper edges some orange/purple RHS N34A. At the base is a little spot of yellow RHS 12A. Midvein is darker RHS N79C. Chirri are RHS N78A with a white tip RHS NN155C; Under surface: Midlobe is purple RHS N78A, in the center a bit lighter RHS N78C. The upper edges red/purple RHS 59A. Lateral lobes are purple RHS N78A. At the base a large white mark RHS NN155C. Lower edge is red/purple RHS 59A. Chirri: medium (about 15 mm). Pestle (Callosities): Length: about 4 mm. Width (not flattened): about 6 mm. Height: about 7 mm. Color: Main color is white RHS NN155C with yellow RHS 12A inside and on the sides with purple/red spots and stripes RHS 64A.

*Sepals*.—Arrangement: Outer whorl comprises 3 sepals. Overall shape: elliptical and weakly cupped. Margin: entire and weakly cupped. Length: about 42 mm. Width: about 25 mm to 35 mm. Apex: oval. Texture: Upper & under surface: smooth and satiny. Color (when fully opened): Upper surface: purple RHS N78B. The base of the lateral sepals is white RHS NN155C with purple/red spots RHS 64A. Under surface: purple RHS N78B.

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 9 mm. Diameter: about 6 mm. Color: RHS N78B.

*Pollinia*.—Quantity: Two. Diameter: about 1 mm. Color: RHS 25A.

*Ovary*.—Length: about 5 mm. Diameter: about 6 mm. Color: white RHS N155C, with some purple RHS N78B.

*Pedicel*.—Length: about 40 mm to 45 mm. Diameter: about 3 mm to 4 mm. Texture: glabrous and smooth. Color: close to the flower purple RHS 75A; close to the raceme RHS 146A; in between RHS N78 B.

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Pacific Point', as illustrated and described herein.

* * * * *